(12) United States Patent
Hwang et al.

(10) Patent No.: US 8,022,050 B2
(45) Date of Patent: Sep. 20, 2011

(54) COMPOUND FOR INHIBITING TRPA1 FUNCTION AND USE THEREOF

(75) Inventors: Sun Wook Hwang, Seoul (KR); Sang-Soo Bang, Gyeonggi-do (KR)

(73) Assignee: Korea University Industry and Academic Collaboration Foundation, Seoul (KR)

( * ) Notice: Subject to any disclaimer, the term of this patent is extended or adjusted under 35 U.S.C. 154(b) by 394 days.

(21) Appl. No.: 12/388,449

(22) Filed: Feb. 18, 2009

(65) Prior Publication Data
US 2010/0137259 A1   Jun. 3, 2010

(30) Foreign Application Priority Data
Nov. 28, 2008   (KR) ..................... 10-2008-0119772

(51) Int. Cl.
*A61K 31/66* (2006.01)
(52) U.S. Cl. ...................................... 514/106; 514/102
(58) Field of Classification Search .................. None
See application file for complete search history.

(56) References Cited

U.S. PATENT DOCUMENTS

| 2007/0196866 A1 | 8/2007 | Patappoutian et al. |
| 2007/0219222 A1 | 9/2007 | Moran et al. |
| 2008/0050750 A1 | 2/2008 | Lee et al. |

FOREIGN PATENT DOCUMENTS

| JP | 20080079528 | 4/2008 |
| KR | 10-2007-0106220 | 11/2007 |
| WO | WO 2005/089206 | 9/2005 |
| WO | WO 2007/073505 | 6/2007 |
| WO | WO 2007/098252 | 8/2007 |
| WO | WO 2008/013861 | 1/2008 |
| WO | WO 2008/129258 | 10/2008 |

OTHER PUBLICATIONS

Petrus, M et al. "A role of TRPA1 in mechanical hyperalgesia is revealed by pharmacological inhibition"; *Molecular Pain* (2007) 3:40.
McNamara, CR et al. "TRPA1 mediates formalin-induced pain"; *PNAS* (2007) 104(33):13525-13530.

*Primary Examiner* — Sreeni Padmanabhan
*Assistant Examiner* — Svetlana M Ivanova
(74) *Attorney, Agent, or Firm* — Greenlee Sullivan P.C.

(57) ABSTRACT

The present invention relates to a TRPA1 activation inhibitor, more precisely a TRPA1 activity inhibitor containing isopentenyl pyrophosphate and a method for inhibiting pain containing the step of administering isopentenyl pyrophosphate to a subject. Isopentenyl pyrophosphate of the present invention can regulate pain caused by TRPA1, so that it can be effectively used for the development of a pain inhibitor which is effective but has less side effects.

4 Claims, 4 Drawing Sheets

COMPOUND FOR INHIBITING TRPA1 FUNCTION AND USE THEREOF

CROSS-REFERENCE TO RELATED APPLICATIONS

This application claims priority under 35 USC 119 (a)-(d) to Korea Application No. 10-2008-0119772 filed on Nov. 28, 2008, the contents of which are hereby incorporated by reference in their entirety.

BACKGROUND OF THE INVENTION

The present invention relates to a TRPA1 activity inhibitor, more precisely isopentenyl pyrophosphate, a compound for suppressing TRPA1 mediated pain by inhibiting TRPA1 activity and a novel use of the same.

TRPA1 (transient receptor potential cation channel, subfamily A, member 1) was first found in 2003 owing to the studies in the fields of human physiology and pharmacology. TRPA1 is activated as it recognizes diverse stimuli such as low temperature stimulus, inflammatory stimulus, and mechanical stimulus, etc. And by the activation of TRPA1, the human body feels pain. TRPA1 belongs to thermoTRP family (temperature-sensitive transient receptor potential ion channels) that is the pain receptor family recognizing temperature and painful stimuli. Researches expect that human pain recognition mechanism can be explained by disclosing functions of TRPA1, the pain receptor, and additionally the pursuing goal of pain relief can be achieved by the development of a TRPA1 regulator.

There is no report on an endogenous pain inhibitor, yet. Studies have been actively going on different types of pain, but mechanisms of pain regulators in vivo have not been disclosed yet. Prostaglandin generated by inflammation and its metabolites and aldehydes are known as pain inducing materials.

To understand basic techniques used for the development of a pain inhibitor based on the TRPA1 specific inhibitor, it is important to understand the characteristics of TRPA1. TRPA1 is an ion channel and its activation makes cations migrate into sensory neurons, changing of cell membrane currents. The changes of cell membrane currents result in the generation of active potential, which is at last transferred to the brain to recognize pain. One of the techniques to measure TRPA1 activation is patch-clamp electrophysiological technique measuring the changes of membrane currents after amplifying thereof. And another technique to measure TRPA1 activation is to measure intracellular calcium level based on the fact that TRPA1 is involved in the migration of cations such as calcium ions. The first technique is superior in sensitivity to the second one, but the second technique is superior in high speed to the first one, so that they are complementary to each other. Such techniques to measure TRPA1 activation can be executed by the support of animal neuron culture technique, cell line culture technique, TRPA1 DNA control and transfection techniques. Various TRPA1 specific inhibitor candidates and a standard activator are administered to TRPA1 over-expressing cells and then inhibiting effect of TRPA1 activation therein is measured to select a proper TRPA1 inhibitor and determine its capacity.

The present inventors constructed a cell line expressing TRPA1 and treated the cell line with isopentenyl pyrophosphate and cinnamaldehyde known as a TRPA1 activator. Then, responses therein were compared. At last the present inventors completed this invention by confirming that isopentenyl pyrophosphate inhibited TRPA1 activity and thus it could be effectively used as an inhibitor of TRPA1 mediated pain.

SUMMARY OF THE INVENTION

It is an object of the present invention to provide a method for inhibiting TRPA1 (transient receptor potential cation channel, subfamily A, member 1) activity using isopentenyl pyrophosphate.

It is another object of the present invention to provide a method for screening a TRPA1 activity inhibitor using isopentenyl pyrophosphate.

It is also an object of the present invention to provide a method for inhibiting pain of a subject using isopentenyl pyrophosphate.

To achieve the above objects, the present invention provides a method for inhibiting TRPA1 (transient receptor potential cation channel, subfamily A, member 1) activity using isopentenyl pyrophosphate.

The present invention also provides a method for screening a TRPA1 activity inhibitor comprising the following steps;

1) constructing a transformant by transfecting a host cell with a plasmid harboring the polynucleotide encoding TRPA1;

2) treating the transformant with TRPA1 specific activator and TRPA1 activity inhibitor candidates as the experimental group, and treating the transformant with TRPA1 specific activator and isopentenyl pyrophosphate as the control;

3) measuring TRPA1 ion channel activities in the experimental group and in the control group of step 2); and 4) comparing the results of step 3) and selecting TRPA1 activity inhibitor candidates from the experimental group that demonstrated lower or similar TRPA1 ion channel activity, compared with the control.

The present invention further provides a method for inhibiting pain containing the step of administering a pharmaceutically effective dose of isopentenyl pyrophosphate to a subject.

Isopentenyl pyrophosphate of the present invention can regulate pain caused by TRPA1, so that it can be effectively used for the development of a pain inhibitor which is effective but has less side effects.

BRIEF DESCRIPTION OF THE DRAWINGS

The application of the preferred embodiments of the present invention is best understood with reference to the accompanying drawings, wherein.

Figure 3A:
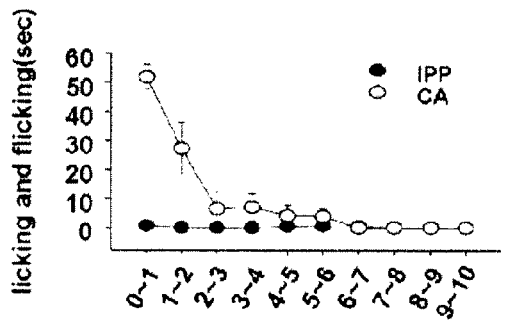
FIG. 3 is a diagram illustrating that pain induced by cinnamaldehyde under normal or inflammatory condition was inhibited by isopentenyl pyrophosphate (CAR: carrageenan, CFA: complete Freund's adjuvant)
Figure 3B:
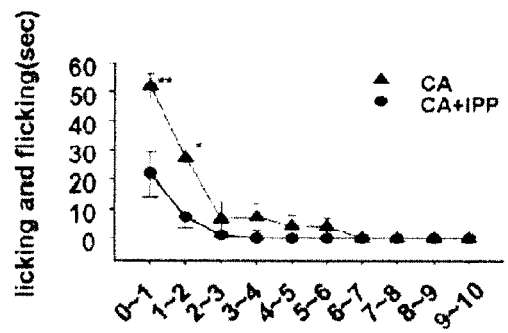
Figure 3C:
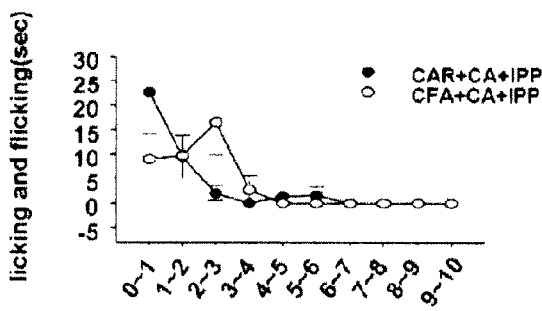
Figure 3D:
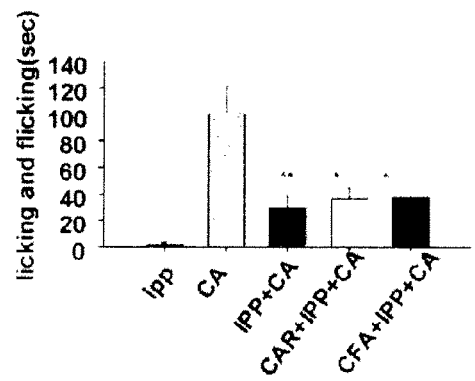

a: 100 µM of isopentenyl pyrophosphate and 300 µM CA;
   b: 300 µM of CA and 300 µM of CA+100 µM of isopentenyl pyrophosphate;
   c: 50 µl of CAR+300 µM of CA+100 µM of isopentenyl pyrophosphate and 10 µl of CFA+300 µM of CA+100 µM of isopentenyl pyrophosphate; and, d: histogram illustrating the results of 10-minute reaction in FIG. 3a-FIG. 3c (The time required was statistically calculated by T-test, for which CA alone was regarded as standard).

Figure 4:
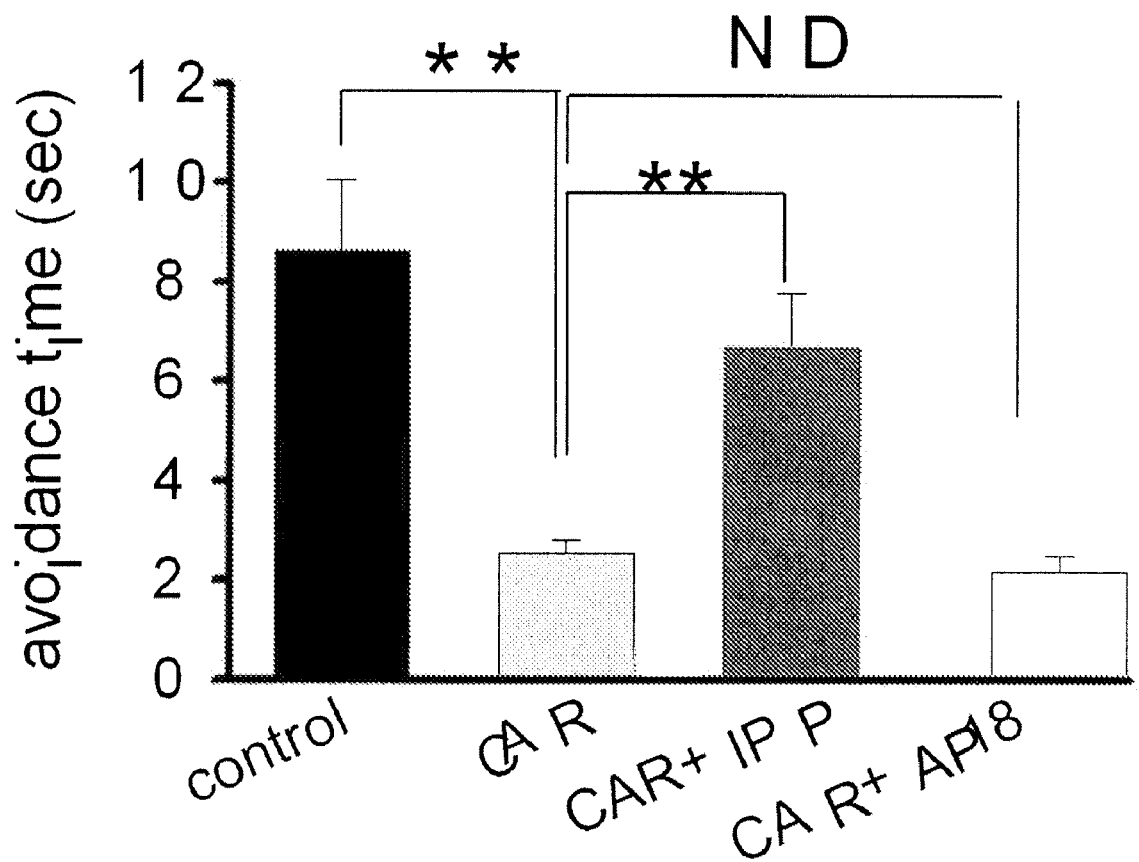

FIG. 4 is a diagram illustrating the changes of avoidance time from temperature stimulus by isopentenyl pyrophosphate under inflammatory condition:

Control: carrageenan not treated group
CAR: carrageenan treated group
CAR+IPP: carrageenan and isopentenyl pyrophosphate treated group
CAR+AP18: carrageenan and AP18 treated group.

DETAILED DESCRIPTION OF THE INVENTION

Hereinafter, the present invention is described in detail.

The present invention provides a method for inhibiting TRPA1 activity containing the step of treating isopentenyl pyrophosphate to isolated sensory neurons expressing TRPA1.

Figure 1:
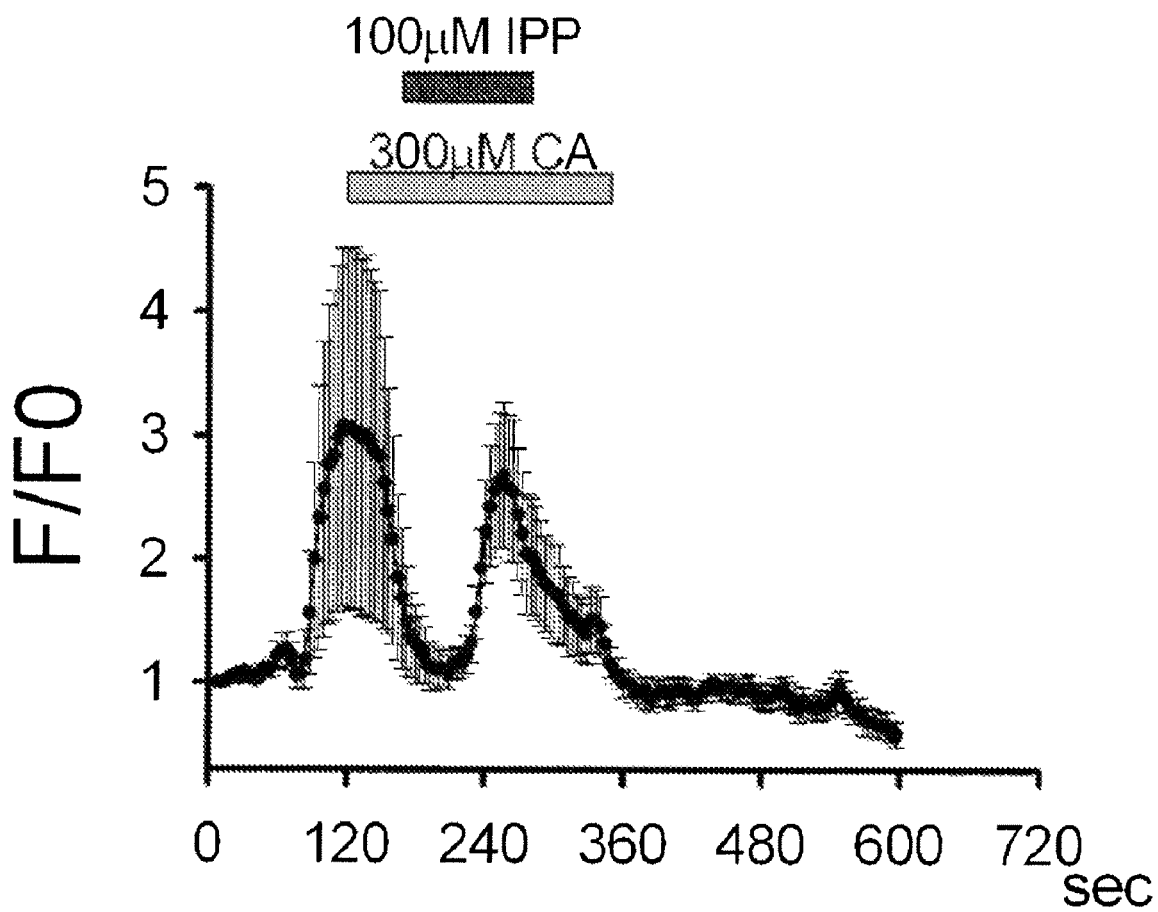
FIG. 1 is a diagram illustrating that TRPA1 specific activity induced by cinnamaldehyde in mTRPA1 cell line was inhibited by isopentenyl pyrophosphate (CA: cinnamaldehyde).
Figure 2:
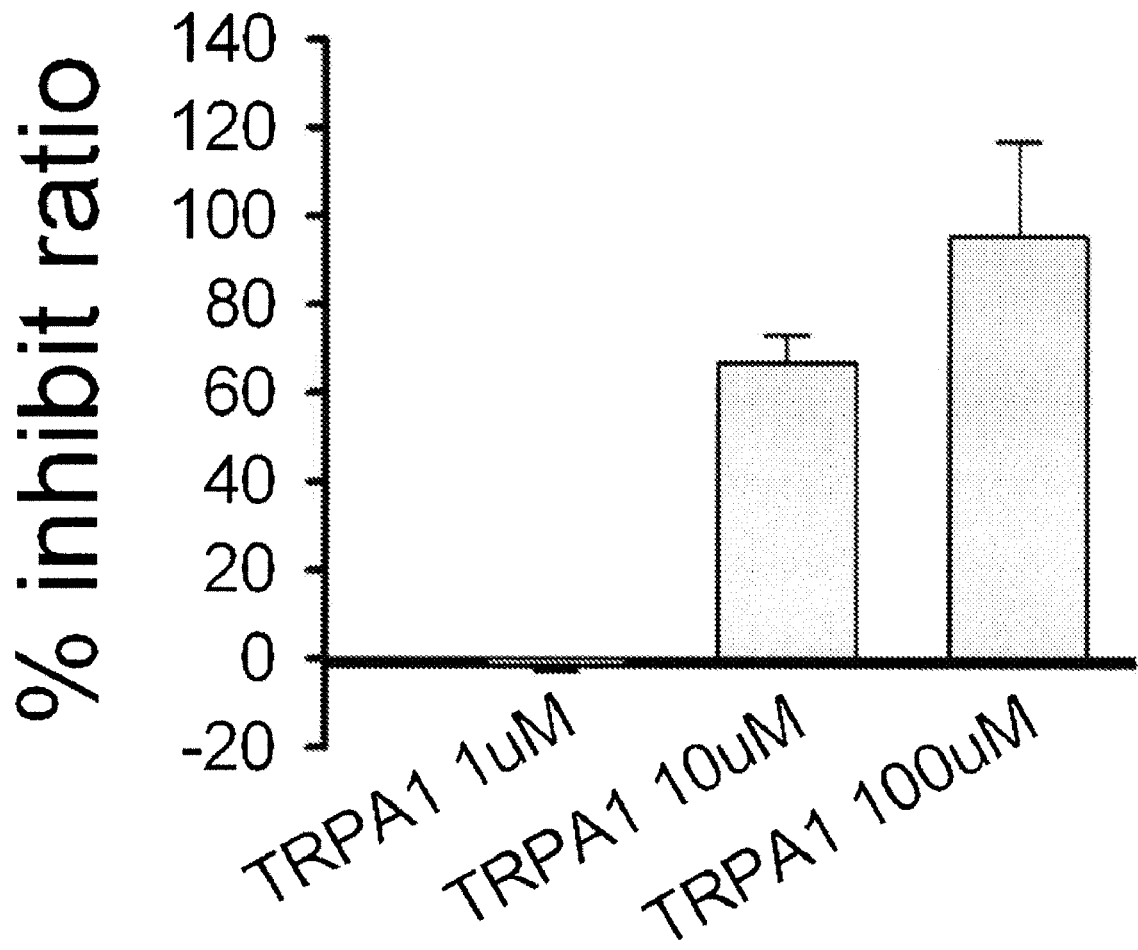
FIG. 2 is a diagram illustrating that TRPA1 activity was specifically inhibited by isopentenyl pyrophosphate in mTRPA1 cell line dose-dependently.

In a preferred embodiment of the present invention, it was confirmed that TRPA1 activity induced by cinnamaldehyde known as a TRPA1 specific activator was inhibited by isopentenyl pyrophosphate dose-dependently (see FIGS. 1 and 2). It was also confirmed that isopentenyl pyrophosphate inhibited TRPA1 mediated pain (see FIG. 3). Therefore, the said isopentenyl pyrophosphate can be effectively used for inhibiting TRPV3 activity.

The preferable concentration of isopentenyl pyrophosphate was 10-100 µM. In a preferred embodiment of the present invention, the TRPA1 inhibitor was confirmed to inhibit TRPA1 activity at micro-molar concentration range (see FIG. 2).

Isopentenyl pyrophosphate of the present invention can be formulated for oral administration, for example powders, granules, tablets, capsules, suspensions, emulsions, syrups and aerosols, and for parenteral administration, for example external use, suppositories and sterile injections, etc.

Solid formulations for oral administration are powders, granules, tablets, capsules, soft capsules and pills. Liquid formulations for oral administration are suspensions, solutions, emulsions and syrups, and the above-mentioned formulations can contain various excipients such as wetting agents, sweeteners, aromatics and preservatives in addition to generally used simple diluents such as water and liquid paraffin. For formulations for parenteral administration, powders, granules, tablets, capsules, sterilized suspensions, liquids, water-insoluble excipients, suspensions, emulsions, syrups, suppositories, external use such as aerosols and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The present invention also provides a method for screening a TRPA1 activity inhibitor comprising the following steps:

1) constructing a transformant by transfecting a host cell with a plasmid harboring the polynucleotide encoding TRPA1;

2) treating the transformant with TRPA1 specific activator and TRPA1 activity inhibitor candidates as the experimental group, and treating the transformant with TRPA1 specific activator and isopentenyl pyrophosphate as the control;

3) measuring TRPA1 ion channel activities in the experimental group and in the control group of step 2); and 4) comparing the results of step 3) and selecting TRPA1 activity inhibitor candidates from the experimental group that demonstrated lower or similar TRPA1 ion channel activity, compared with the control.

In a preferred embodiment of the present invention, it was confirmed that TRPA1 activity induced by cinnamaldehyde known as a TRPA1 specific activator was inhibited by isopentenyl pyrophosphate dose-dependently (see FIGS. 1 and 2). It was also confirmed that isopentenyl pyrophosphate was inhibited TRPA1 mediated pain in animal models (see FIG. 3). Therefore, the said isopentenyl pyrophosphate can be effectively used for the screening of a TRPA1 activity inhibitor.

The host cell herein is preferably any cell line that can be used for the study of calcium channel activity and high throughput screening, for example HEK, CHO, HeLa, and RBL-2H3, but not always limited thereto.

The TRPA1 specific activator of step 2) is cinnamaldehyde or acetaldehyde.

The measuring of ion channel activity of step 3) can be performed by whole cell voltage clamp technique or calcium imaging.

The preferable concentration of isopentenyl pyrophosphate is 0.1-100 µM.

The preferable concentration of isopentenyl pyrophosphate is 10-100 µM. In a preferred embodiment of the present invention, the TRPA1 inhibitor was confirmed to inhibit TRPA1 activity at micro-molar concentration range (see FIG. 2).

The present invention also provides a method for inhibiting pain containing the step of administering a pharmaceutically effective dose of isopentenyl pyrophosphate to a subject.

In a preferred embodiment of the present invention, it was confirmed that isopentenyl pyrophosphate inhibited TRPA1 mediated pain in animal models (see FIG. 3 and FIG. 4). So, the said isopentenyl pyrophosphate can be effectively used as a composition for inhibiting pain.

The pain herein is mediated by TRPA1 activity.

The subject herein is one of vertebrates and preferably mammals and more preferably selected from such test animals as rats, rabbits, guinea pigs, hamsters, dogs and cats, and most preferably apes such as chimpanzees and gorillas. The composition of the present invention can be administered orally or parenterally. For example the possible administration pathway can be oral administration, rectal administration, intravenous injection, intramuscular injection, hypodermic injection, intrauterine injection or intracerebroventricular injection. The composition for inhibiting pain of the present invention can be administered alone or treated together with surgical operation, hormone therapy, chemo-therapy and biological regulators.

The effective dosage of the composition of the present invention can be determined by those in the art according to condition and weight of a patient, severity of a disease, type of a drug, administration pathway and duration. Preferably, the composition of the present invention can be administered by 0.0001-100 mg/kg per day, and more preferably by 0.001-100 mg/kg per day. The administration frequency is once a day or a few times a day.

The composition for inhibiting pain can include, in addition to isopentenyl pyrophosphate, one or more effective ingredients having the same or similar function to isopentenyl pyrophosphate. The composition of the present invention preferably includes isopentenyl pyrophosphate by 0.0001-10 weight % and more preferably 0.001-1 weight % for the total weight of the composition.

The composition of the present invention can additionally include generally used carriers, excipients, disintegrating agents, sweetening agents, lubricants, flavors and diluents. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. The disintegrating agent is exemplified by sodium carboxy methyl starch, crospovidone, croscarmellose sodium, alginic acid, calcium carboxymethyl cellulose, sodium carboxymethyl cellulose, chitosan, guar gum, low-substituted hydroxypropyl cellulose, magnesium aluminum silicate, polacrilin potassium, etc.

The composition for inhibiting pain of the present invention can be provided as a pharmaceutical composition. The pharmaceutical composition of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1-90 weight part to the pharmaceutical composition.

The composition for inhibiting pain of the present invention can be provided as a composition for health food.

Isopentenyl pyrophosphate of the present invention can be used as food additive. In that case, isopentenyl pyrophosphate can be added as it is or as mixed with other food components according to the conventional method. The mixing ratio of active ingredients can be regulated according to the purpose of use (prevention or health enhancement). In general, to produce health food or beverages, isopentenyl pyrophosphate is added preferably by 0.2-20 weight % and more preferably by 0.24-10 weight %. However, if long term administration is required for health and hygiene or regulating health condition, the content can be lower than the above but higher content can be accepted as well since isopentenyl pyrophosphate has been proved to be very safe.

The health food of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 weight part and more preferably 0.02-0.03 weight part in 100 weight part of the health food of the present invention.

The food herein is not limited. For example, isopentenyl pyrophosphate of the present invention can be added to meat, sausages, bread, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

In addition to the ingredients mentioned above, the health food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The health food of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 001-0.1 weight part per 100 weight part of the health food of the present invention.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Construction of Cell Lines Transfected with TRPA

HEK293T cell line (ATCC CRL-11268) was transiently transfected with plasmid DNA containing polynucleotide encoding rTRPA1 (SEQ. ID. NO: 1).

Particularly, the HEK293T cell line was transiently transfected with 3 μg/35 mm dish of pcDNA5/FRT vector containing polynucleotide encoding mTRPA1, and 600 ng/well of pCDNA3 (Invitrogen Corp., USA; containing green fluorescent protein (GFP) cDNA) using Fugene6 (Roche Diagnostics, USA) according to manufacturer's instruction. The transformed cells were cultured in DMEM/F12 medium containing 10% FBS and 1% penicillin/streptomycin in a $CO_2$ incubator for 24 hours. The cells were smeared on poly-L-lysine-coated glass coverslips, followed by further culture for 10-24 hours.

Example 2

Statistical Treatment

All the results of examples were statistically analyzed by two-tailed, unpaired Student's-t-test and the results were presented by mean±S.E.M. (**$p<0.01$, and *$p<0.05$).

Example 3

TRPA1 Activity Inhibition by TRPA1 Inhibitor

<3-1> Treatment of Compounds

The mTRPA1 transfected cell line (n=73) prepared in Example 1 was treated with 300 μM of cinnamaldehyde (CA; MP Biomedicals, USA), during which 100 μM of isopentenyl pyrophosphate (Biomol, USA) was treated for a certain period of time. Stock solutions were made using water or ethanol, and were diluted with test solutions before use.

<3-2> Measurement of Intracellular Calcium Level Changes by Calcium Imaging

Calcium imaging was performed with the transfected cell line treated by the method of Example <3-1>.

Particularly, the transfected cell line of Example <3-1> was loaded with Fluo-3AM (5 μM; Sigma Aldrich, USA) in the bath solution (140 mM NaCl, 5 mM KCl, 2 mM $CaCl_2$, 1 mM MgCl$_2$, 10 mM HEPES; adjusted to pH 7.4 with NaOH) containing 0.02% pluronic acid (Invitrogen, USA) at 37° C. for 1 hour. Calcium imaging was performed with LSM5 Pascal confocal microscope (Carl Zeiss, Germany), and time-lapse images (excitation 488 nm/emission 514 nm) were collected every 3 seconds using Carl Zeiss ratio tool software (Carl Zeiss, Germany). Mean value curve of calcium influx responses was made by Hill plot.

As a result, as shown in FIG. 1, TRPA1 activity induced by cinnamaldehyde was inhibited by isopentenyl pyrophosphate.

Example 4

TRPA1 Activity Over TRPA1 Inhibitor Concentration

The TRPA1 transfected cell line (n=73-127) prepared in Example 1 was treated with 300 μM of CA and 1, 10 and 100 μM of isopentenyl pyrophosphate. Calcium imaging was performed with the transfected cell line.

As a result, as shown in FIG. 2, TRPA1 activity induced by cinnamaldehyde was inhibited by isopentenyl pyrophosphate in the mTRPA1 cell line dose-dependently.

Example 5

Pain Relieving Response by TRPA1 Inhibitor Examined by Animal Test

<5-1> Inducement of Inflammatory Sensitization

Inflammatory sensitization by isopentenyl pyrophosphate was investigated. Particularly, 50 μl of 1% carrageenan (CAR, Sigma Aldrich, USA) was injected to the right hind paws of mice 3 hours before the isopentenyl pyrophosphate injection or 10 μl of CFA (complete Freund's adjuvant; Sigma Aldrich, USA) was injected 24 hours before the isopentenyl pyrophosphate injection. At this time, 10 mM cinnamaldehyde was diluted in PBS containing 0.5% Tween 80 for injection. Before the experiment, the mice were adapted for one hour to the experimental environment. 10 μl of vehicle (saline containing 3% DMSO and 0.5% Tween 80) alone or 10 μl of vehicle containing isopentenyl pyrophosphate (3 mM) was injected to the right hind paws of the mice.

<5-2> Investigation of Acute Licking/Flicking Behaviors

The time spent for the hind paw licking/flicking behaviors in mice were measured according to the method of Bandell M, et al. (*Neuron* 41:849-857, 2004) and Moqrich A, et al. (*Science* 307:1468-1472, 2005), for 10 minutes.
  Control: non-treatment;
  Experimental group 1. 100 μM of isopentenyl pyrophosphate;
  Experimental group 2. 300 μM of CA;
  Experimental group 3. 300 μM of CA+100 μM of isopentenyl pyrophosphate;
  Experimental group 4. 50 μl of CAR+300 μM of CA+100 μM of isopentenyl pyrophosphate; and,
  Experimental group 5. 10 μl of CFA+300 μM of CA+100 μM of isopentenyl pyrophosphate.

As a result, as shown in FIG. 3, unlike isopentenyl pyrophosphate, cinnamaldehyde increased the time spent for the behaviors (FIG. 3a), and co-treatment of cinnamaldehyde and isopentenyl pyrophosphate reduced the time spent for the behaviors (FIG. 3b).

When carrageenan or CFA was injected to cause inflammation, the time spent for the behaviors which had been increased by cinnamaldehyde was also reduced by isopentenyl pyrophosphate (FIG. 3c). The result of 10 minute-reaction induced in animals was also consistent with the result shown in FIG. 3d.

In addition, when CAR and CFA alone were injected and when isopentenyl pyrophosphate alone was treated, the time spent for the behaviors was not increased (no data).

<5-3> Analysis of Sensitivity to Thermal Stimulation

To investigate inhibition of inflammatory sensitization induced by isopentenyl pyrophosphate, 10 μl of 0.1% carrageenan (CAR; Sigma Aldrich, USA) was injected into the right hind paws of mice three hours before the isopentenyl pyrophosphate injection. 10 μl of isopentenyl pyrophosphate was injected into the experimental group at the concentration of 1 mM. Equal amount of AP18 (Biomol, USA), the TRPA1 specific inhibitor, was injected into the positive control. Avoidance time was measured by using thermal stimulator (Ugo basile plant test, Italy). Each group was composed of 5 mice and beam injection was performed four times, which were averaged. As a result, as shown in FIG. 4, the mice injected with carrageenan were more sensitive to thermal stimulation than the mice not-treated. In the meantime, the mice co-treated with carrageenan and isopentenyl pyrophosphate (IPP) of the present invention demonstrated significantly reduced sensitivity against thermal stimulation. Particularly, AP18 known as a TRPA1 specific inhibitor exhibited almost no effects. On the other hand, isopentenyl pyrophosphate of the present invention demonstrated significant effect, suggesting that it had excellent pain relieving effect, compared with the conventional TRPA1 inhibitors.

The Manufacturing Examples of the composition for the present invention are described hereinafter.

Manufacturing Example 1

Preparation of Pharmaceutical Formulations

<1-1> Preparation of Powders

| | |
|---|---|
| Isopentenyl pyrophosphate | 2 g |
| Lactose | 1 g |

Powders were prepared by mixing all the above components, which were filled in airtight packs according to the conventional method for preparing powders.

<1-2> Preparation of Tablets

| | |
|---|---|
| Isopentenyl pyrophosphate | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Isopentenyl pyrophosphate | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Isopentenyl pyrophosphate | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Isopentenyl pyrophosphate | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2

Preparation of Dairy Products

5~10 weight part of isopentenyl pyrophosphate of the present invention was added to milk. Health enhancing dairy products such as butter and ice cream were prepared with the milk mixture according to the conventional method.

Manufacturing Example 3

Preparation of Beverages

<3-1> Preparation of Health Beverages

| | |
|---|---|
| Isopentenyl pyrophosphate | 1000 mg |
| Citric acid | 1000 mg |
| Oligosaccharide | 100 g |
| Maesil (*Prunus mume*) Extract | 2 g |
| Taurine | 1 g |
| Purified water | up to 900 Ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages. The constituents appropriate for favorite beverages were mixed according to the preferred mixing ratio but the composition ratio can be adjusted according to regional and national preferences, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for inhibiting pain comprising the step of administering a pharmaceutically effective dose of isopentenyl pyrophosphate to a subject.

2. The method according to claim 1, wherein the pain results from TRPA1 activation.

3. The method according to claim 1, wherein the isopentenyl pyrophosphate is administered to a subject in the form of a pharmaceutical composition.

4. The method according to claim 1, wherein the isopentenyl pyrophosphate is administered to a subject in the form of health food.

* * * * *

```
                       SEQUENCE LISTING

<160> NUMBER OF SEQ ID NOS: 1

<210> SEQ ID NO 1
<211> LENGTH: 4263
<212> TYPE: DNA
<213> ORGANISM: Mus musculus

<400> SEQUENCE: 1
gcgccagccg gcgtccaggt ggagtcaatg aagcgcggct tgaggaggat tctgctcccg        60
gaggaaagga aggaggtcca gggcgttgtc tatcgcggcg tcggggaaga catggactgc       120
tccaaggaat cctttaaggt ggacattgaa ggagatatgt gtagattaga agacttcatc       180
aagaaccgaa gaaaactaag caaatatgag gatgaaaatc tctgtcctct gcatcacgca       240
gcagcagaag gtcaagttga actgatggaa ctgatcatca atggttcttc gtgtgaagtg       300
ctgaatataa tggatggtta tggaaatacc ccactgcatt gtgctgcaga aaaaaatcaa       360
gttgaaagtg taaagtttct tctcagccaa ggagcaaatc caaacctccg aaatagaaac       420
atgatgtcac cccttcacat agctgtgcat ggcatgtaca acgaagtgat caaggtgttg       480
actgagcaca aggccactaa catcaattta gaaggagaga atgggaacac ggctttgatg       540
tccacgtgtg ccaaagacaa cagtgaagct ttgcaaattt tgttagaaaa aggagctaag       600
ctgtgtaaat caaataagtg gggagactac cctgtgcacc aggcagcatt ttcaggtgcc       660
aaaaaatgca tggaattaat cttagcatat ggtgaaaaga acggctacag cagggagact       720
cacattaatt ttgtgaatca caagaaagcc agccctctcc acctagcagt tcaaagcgga       780
```

```
gacttggaca tgattaagat gtgcctggac aacggtgcac acatcgacat gatggagaat    840
gccaaatgca tggccctcca ttttgctgca acccagggag ccactgacat cgttaagctc    900
atgatctcat cctataccgg aagtagtgat attgtgaatg cagttgatgg caatcaggag    960
accctgcttc acagagcctc gttatttgat caccatgacc tggcagaata cctaatatca   1020
gtgggagcag acatcaacag cactgattct gaaggacgct ctccacttat tttagcaaca   1080
gcttctgcat cctggaacat tgtgaatttg ctcctctgta aaggtgccaa agtagacata   1140
aaagatcatc ttggacgtaa cttttttgcat ttgactgtgc agcagcctta tggactaaga   1200
aatttgcggc ctgagtttat gcagatgcaa cacatcaaag agctggtgat ggatgaagac   1260
aatgacggat gcacacctct ccattatgcc tgtaggcagg gggttcctgt ctctgtaaat   1320
aacctccttg gcttcaatgt gtccattcat agcaaaagta aagataagaa gtcgcccctg   1380
cattttgcag ccagttatgg gcgcatcaat acatgtcaga gacttctgca agacataagt   1440
gatacgaggc ttttgaatga aggggatctc catgggatga cccctctcca cctggcagca   1500
aaaaatgggc atgataaagt cgttcaactc cttctgaaga aggggccttt atttctcagt   1560
gaccacaatg gctggactgc tttgcatcac gcctccatgg gtgggtacac tcagaccatg   1620
aaggtcattc ttgatactaa cttgaaatgc acagaccgac tagatgaaga agggaacaca   1680
gcactccact ttgcagcacg ggaaggccat gccaaggctg ttgcaatgct tttgagctac   1740
aatgctgaca tcctcctgaa caagaagcaa gcttcctttc tgcatattgc cctgcacaat   1800
aagcgcaagg aagtggttct cacaaccatc agaaataaaa gatgggatga gtgtcttcaa   1860
gttttcactc ataattctcc aagcaatcga tgtccaatca tggagatggt agaatacctc   1920
cccgagtgca tgaaagttct tttagatttc tgcatgatac cttccacaga agacaagtcc   1980
tgtcaagact accatattga gtataatttc aagtatctcc aatgcccatt atccatgacc   2040
aaaaaagtag cacctaccca ggatgtggta tatgagcctc ttacaatcct caatgtcatg   2100
gtccaacata accgcataga actcctcaac caccctgtgt gtagggagta cttactcatg   2160
aaatggtgtg cctatggatt cagagcccat atgatgaacc taggatctta ttgtcttggt   2220 ctcatacca tgaccttct tgttgtcaaa atacagcctg gaatggcctt caattctact   2280
ggaataatca atggaactag tagtactcat gaggaaagaa tagacactct gaattcattt   2340
ccaataaaaa tatgtatgat tctagttttt ttatcaagta tatttggata ttgcaaagaa   2400
gtgatccaaa ttttccaaca gaaaaggaat tacttcctgg attacaacaa tgctctggaa   2460
tgggttatct atacaactag tatcatcttc gtgttgccct tgttcctcaa catcccagcg   2520
tatatgcagt ggcaatgtgg agcaatagcg atattcttct actggatgaa cttcctactg   2580
tatcttcaaa ggtttgagaa ctgtggaatt ttcattgtta tgttggaggt gatttttaaa   2640
acattgctga atcgaccgg agtgtttatc ttcctcctac tggcttttgg cctcagcttt   2700
tatgttctcc tgaatttcca agatgccttc agcaccccat tgctttcctt aatccagaca   2760
ttcagtatga tgctaggaga catcaattat cgagatgcct tcctagaacc attgtttaga   2820
aatgagttgg catacccagt cctgaccttt gggcagctta ttgccttcac aatgtttgtc   2880
ccaattgttc tcatgaactt actgattggc ttggcggttg gggacattgc tgaggtccag   2940
aagcatgcgt cattgaagag gattgctatg caggtggaac ttcataccaa cttagaaaaa   3000
aagctgccac tctggtactt acgcaaagtg gatcagaggt ccaccatcgt gtatccaaat   3060
agacccaggc acggcaggat gctacggttt tttcattact ttcttaatat gcaagaaaca   3120
cgacaagaag taccaaacat tgacacatgc ttggaaatgg aaatattgaa acagaaatat   3180
```

-continued

```
cggctgaagg acctcacttc cctcttggaa aagcagcatg agctcatcaa actcatcatc    3240
cagaagatgg agatcatctc agagacagaa gatgaagata accattgctc tttccaagac    3300
aggttcaaga aggagaggct ggaacagatg cacagcaagt ggaattttgt cttaaacgca    3360
gttaagacta aaacacattg ttctattagc cacccggact tttagttctg tgtcttatgg    3420
gagtgggaga ctgctttaca tacttatttc agtgaatttc agtttggaaa agagcaaaga    3480
aacagaaagt tgactaacat tgctgcatgg agatcctagt tcctgcaacc tcacccatac    3540
atatgctcat atttcctgtc aattactatg tattgagaag atcctttctg acatgttcaa    3600
tttgaacatg aaggatagtc tctttcgagt gaataaaaac cagggttgtt ggaatgcata    3660
ttatggagga taagaattaa tgtaactatt aaggcagaac acaactacat aatacaagat    3720
gcatataatt ccaagtatta tatttaatct cctaccatgt taaaccttcc tgtgttataa    3780
cctgtctggg acactataat ctctgttcct actatgatta gatcatagtc tcaccctcct    3840
cgtcccatca cacatgacat catttgagc cacatgacag aagtcctagt tagtagactg    3900
tgataagtat gaatgttaca atagaaatgt gttcccttag tgttcatcag ttgtgatggt    3960
ttaaatgaga aacgttgccc acagactcat acatttaaac ccttagtccc agttgttgct    4020
gctgcttagg ggggccacac agccttgctt gctctctcct ttctgagtgt ggagagaaat    4080
gtgatcagta agactcctgc tcctgctgcc atgctcttta ttccattatg gacttcttct    4140
gaaactgcaa gcagaaattc actgttcctt cctcaaattt cttttggtca tggtattata    4200
tcatagcaac agaaactaac ttatgtacca atggtcttaa taaagaataa agcctgtaca    4260
gtc                                                                 4263
```